(12) United States Patent
Gordon et al.

(10) Patent No.: US 7,277,749 B2
(45) Date of Patent: Oct. 2, 2007

(54) TREATMENTS FOR SNORING USING INJECTABLE NEUROMUSCULAR STIMULATORS

(75) Inventors: David C. Gordon, Grand Forks, ND (US); Gerald E. Loeb, South Pasadena, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 607 days.

(21) Appl. No.: 10/758,366

(22) Filed: Jan. 15, 2004

(65) Prior Publication Data

US 2004/0153127 A1    Aug. 5, 2004

Related U.S. Application Data

(60) Provisional application No. 60/440,175, filed on Jan. 15, 2003.

(51) Int. Cl.
*A61N 1/00* (2006.01)

(52) U.S. Cl. .............. 607/2; 607/42; 607/62; 600/380

(58) Field of Classification Search ........... 607/2, 607/42, 134, 62; 128/848; 600/380
See application file for complete search history.

(56) References Cited

U.S. PATENT DOCUMENTS

| | | | |
|---|---|---|---|
| 2,711,729 A | 6/1955 | Hofmann |
| 3,773,051 A | 11/1973 | Holcomb et al. |
| 3,796,221 A | 3/1974 | Hagfors |
| 3,924,641 A | 12/1975 | Weiss |
| 4,220,142 A | 9/1980 | Rosen et al. |
| 4,506,666 A | 3/1985 | Durkan |
| 4,612,934 A | 9/1986 | Borkan |
| 4,827,935 A | 5/1989 | Geddes et al. |
| 4,830,008 A | 5/1989 | Meer |
| 5,158,080 A | 10/1992 | Kallok |
| 5,178,156 A | 1/1993 | Takishima et al. |
| 5,190,053 A | 3/1993 | Meer |
| 5,281,219 A | 1/1994 | Kallok |
| 5,284,161 A | 2/1994 | Karell |

(Continued)

OTHER PUBLICATIONS

Li et al "Pharyngoscopic observation during sleep in patients with obstructive sleep apnea syndrome" Zhonghua Er Bi Yan Hou Ke Za Zhi. Feb. 1999; 34(1):38-40 abstract.*

(Continued)

*Primary Examiner*—Mark Bockelman
(74) *Attorney, Agent, or Firm*—McDermott Will & Emery LLP

(57) ABSTRACT

Many individuals generate excessively loud snoring during their sleep, often to the point where others cannot tolerate sleeping in the same room with them. Most cases of snoring are caused by excessive bulk and flaccidity of soft tissues of the palate and uvula that vibrate as air flows past them. These palate and uvula contain muscles whose contractions can stiffen and displace the soft tissues so that they do not vibrate. The invention provides electrical stimulation that causes the oropharyngeal muscles to contract during sleep using one or more microstimulators injected into or near these muscles or the nerves which innervate them. The invention also provides methods of determining the anatomical structures implicated in snoring and testing such locations for effective placement and stimulation of muscle contraction to decrease the frequency or magnitude of snoring.

47 Claims, 6 Drawing Sheets

U.S. PATENT DOCUMENTS

| | | |
|---|---|---|
| 5,522,862 A | 6/1996 | Testerman et al. |
| 5,540,731 A | 7/1996 | Testerman |
| 5,540,732 A | 7/1996 | Testerman |
| 5,540,733 A | 7/1996 | Testerman et al. |
| 5,549,655 A | 8/1996 | Erickson |
| 5,591,216 A | 1/1997 | Testerman et al. |
| 5,678,535 A | 10/1997 | DiMarco |
| 5,725,564 A | 3/1998 | Freed et al. |
| 5,792,067 A | 8/1998 | Karell |
| 5,891,185 A | 4/1999 | Freed et al. |
| 5,911,218 A | 6/1999 | DiMarco |
| 5,987,359 A | 11/1999 | Freed et al. |
| 6,099,479 A | 8/2000 | Christopherson et al. |
| 6,125,300 A | 9/2000 | Weijand et al. |
| 6,132,384 A | 10/2000 | Christopherson et al. |
| 6,198,870 B1 | 3/2001 | Kubota et al. |
| 6,212,435 B1 | 4/2001 | Lattner et al. |
| 6,250,307 B1 | 6/2001 | Conrad et al. |
| 6,269,269 B1 | 7/2001 | Ottenhoff et al. |
| 6,273,859 B1 | 8/2001 | Remmers et al. |
| 6,314,324 B1 | 11/2001 | Lattner et al. |
| 6,345,202 B2 | 2/2002 | Richmond et al. |
| 6,360,740 B1 | 3/2002 | Ward et al. |
| 6,411,852 B1 | 6/2002 | Danek et al. |
| 6,636,767 B1 * | 10/2003 | Knudson et al. .............. 607/42 |
| 2002/0049479 A1 | 4/2002 | Pitts |

OTHER PUBLICATIONS

Loeb et al. "Development of Asynchronous Intralingual Electrical Stimulation to Treat Obstructive Sleep Apnea", Alfred E. Mann Institute for Biomedical Engineering, University of Southern California, (Sep. 17, 2003), presented at Proceedings of the 25th Annual EMBS International Conference, Cancun, Mexico.

* cited by examiner

TREATMENTS FOR SNORING USING INJECTABLE NEUROMUSCULAR STIMULATORS

CROSS-REFERENCE TO RELATED APPLICATIONS

This application claims priority to U.S. Provisional Patent Application 60/440,175 filed Jan. 15, 2003, and incorporates the contents in its entirety.

FIELD OF THE INVENTION

The present invention relates to a system and method for treating snoring, and more particularly methods for determining anatomical structures implicated in snoring and using implantable microstimulators to treat snoring.

BACKGROUND

Snoring can be defined as noisy respiratory sounds while sleeping. People who snore do not usually make snoring sounds when breathing awake in the same posture that is associated with snoring when asleep. That is because the awake person has conscious control of various muscles whose mechanical action tenses and shapes the upper airway so as to prevent the vibrations that cause snoring to occur. During sleep, the motor neurons that control most skeletal muscles are inhibited from sending commands to activate those muscles. The resulting flaccid muscle tone permits soft tissue to sag into the airway and consequently snoring to occur.

Snoring may also occur because the airway is constricted, creating turbulence, and/or when the soft tissues are unusually large, soft and easily vibrated. Snoring is particularly common and severe in males, older people, and obese people, but it can occur in virtually anyone. Predisposing factors include obesity with accumulation of adipose tissue in the airway and congenital narrowing of the upper airway. Snoring may occur in any position but is most pronounced when sleeping in a supine position in which gravity causes soft tissues to fall against the back of the airway.

The sounds of snoring are generated by vibration of soft tissues in the upper airway, such as the soft palate, uvula, tongue, lips, posterior and lateral pharyngeal wall and epiglottis. However, the soft palate and uvula are most commonly implicated.

Many treatments for excessively loud snoring have been proposed, but few are in common use because of various disadvantages and limitations in effectiveness. Treatments include mechanical devices to control body posture, mechanical appliances worn in the mouth and on the jaw, electrical stimulators applied to the mucosa of the oral cavity, surgical remodeling of the oropharynx, sound detectors to awaken the offending snorer, and acoustic cancellation techniques to reduce the sounds heard by companions. Many of these techniques have only limited effectiveness or are applicable only to certain sources of snoring. Those that are effective have various disadvantages that include physical discomfort, interference with the normal sleep of the patient and reoccurrence of snoring over time.

Muscles can be electrically stimulated artificially to contract directly or indirectly by activating the neurons that innervate them. Such stimulation has been applied to reanimate paralyzed limbs, but it has not been feasible to apply to oropharyngeal muscles with the previously available technologies. Stimulation of limb muscles has been accomplished by applying transcutaneous electrodes to the surface of the skin, by inserting percutaneous wires into the muscles and by surgically implanting electrodes in or on muscles and nerves, which electrodes are connected by leads to a central stimulus pulse generator similar to a cardiac pacemaker. More recently, wireless microstimulators have become available that are small enough to be injected into the body where they receive electrical power and/or command signals by inductive coupling from a radio-frequency electromagnetic field generated outside the body.

The muscles of the oropharynx and their motor nerves are small and difficult to access surgically. Electrical stimulation pulses applied to the muscles transcutaneously via the mucosa of the oropharynx causes unpleasant sensations as a result of activation of its many sensory nerve endings.

While snoring may not wake the subjects themselves, it is often very problematic because the noise disturbs the sleep of others in the vicinity, such as a spouse or roommate. Therefore, effective methods and devices for the treatment of snoring are desirable.

SUMMARY OF THE INVENTION

The present invention may include a method for treating snoring comprising monitoring the airway passage of a patient during sleep to identify at least one anatomical structure in the airway passage that vibrates during snoring; implanting at least one microstimulator in the proximity of at least one anatomical structure in the airway passage that vibrates during snoring; and energizing the microstimulator to deliver an electrical stimulation to the anatomical structure to cause at least one muscle to contract and reduce the vibrations of the airway passage.

The invention may also include inserting a distal end of a scope such that the distal end is located in an upper airway of the patient and monitoring the airway passage during sleep.

The invention may also include inserting a distal tip of an insertion tool into the anatomical structure, wherein the microstimulator is located in a lumen of the insertion tool, and activating the insertion tool to eject the microstimulator from the insertion tool, and removing the insertion tool from the anatomical structure.

The invention may also include delivering an electrical stimulation to the anatomical structure prior to implantation and observing the anatomical structure for a decrease in vibration.

The invention may also include inserting a distal tip of an insertion tool into an anatomical structure, applying an electrical current to at least the distal tip of the insertion tool, and delivering an electrical current to the anatomical structure.

The invention may also include inserting a distal tip of an insertion tool into the anatomical structure, wherein the microstimulator is located in a lumen of the insertion tool, and energizing the microstimulator located within the lumen of an insertion tool.

The invention may also include testing the microstimulator by emitting electrical stimulations at a plurality of intensities, and observing the anatomical structure to determine the intensity which decreases the vibration of the anatomical structure. The present invention may further include a method wherein the electrical stimulation is of an intensity from about 8 to about 800 nC.

The present invention may further include energizing the microstimulator at a selected frequency to deliver an electrical stimulation to the anatomical structure to cause at least one muscle to contract and reduce the vibrations of the airway passage. The present invention may further include a method wherein the frequency is about 1 to about 30 pulses per second.

The present invention may further provide interruptions of a selected duration and period in the electrical stimulation to permit the at least one muscle to relax. The present invention may further include a method wherein the duration of the interruption is from about 0.2 to about 2 seconds and the selected period is from about 5 to about 20 seconds.

The present invention may further comprise sensing when snoring is occurring; and generating an electrical stimulus from the microstimulator to contract an oropharyngeal muscle, in response to sensing snoring. The present invention may further sense snoring by detecting mechanical vibrations or acoustically detecting sounds generated by vibrating at least one anatomical structure in the airway passages.

The present invention may further include a method wherein the energizing includes delivering a control signal to a pair of electrodes, wherein the microstimulator includes the pair of electrodes.

The present invention may further include a method wherein the anatomical structure is selected from the group comprising the soft palate or the uvula. The present invention may further include a method wherein the anatomical structure is a muscle selected from the group comprising: palatoglossus, palatopharyngeal, musculus uvulae, genioglossus, geniohyoid, levator palati or tensor palati. The present invention may further include a method wherein the anatomical structure is a branch or terminal of a nerve selected from the group comprising: vagus X, hypoglossal, vagus pharyngeal branch, V3 branch trigeminal nerve.

The invention may further comprise implanting a second microstimulator proximate to at least a second anatomical structure, different from the at least one anatomical structure. The present invention may further include a method wherein at least one anatomical structure and a second anatomical structure are muscle pairs selected from the group comprising: geniohyoid and genioglossus; tensor palati and palatoglossus; tensor palati and musculus uvulae.

The present invention may further include a method wherein at least one of the microstimulators includes a sensor and a telemeter configured to generate a signal indicative of a sensed condition, and at least one of the microstimulators includes a circuitry configured to generate an electrical stimulation pulse.

The present invention may further include a method of treating snoring comprising implanting a microstimulator within at least one of the soft palate or the uvula; and activating the microstimulator to deliver an electrical stimulation to at least one of the soft palate or the uvula to cause at least one muscle to contract.

The present invention may further include a method wherein the microstimulator includes an electrical circuit configured to generate an electrical stimulus and a pair of electrodes configured to apply the electrical stimulus to the at least one of the soft palate or uvula. The present invention may further transmit from a controller to the microstimulator power, control signals, or power and control signals.

The present invention may further transmit an acknowledgement signal from the microstimulator to a controller, wherein the acknowledgement signal indicates that the microstimulator has received a control signal from a controller.

The method of the present invention may further activate the microstimulator in a temporal pattern to deliver the electrical stimulation to at least one of the soft palate or the uvula to cause at least one muscle to contract, wherein the temporal pattern includes periods of an absence of electrical stimulation to permit the at least one muscle to cease from contracting.

The method of the present invention may further test the microstimulator by emitting electrical stimulations at a plurality of intensities, and observe at least one of the uvula or soft palate to determine the intensity which decreases the vibration of the uvula or soft palate. The present invention may further include a method wherein the electrical stimulation is of an intensity from about 8 to about 800 nC.

The method of the present invention may further comprise sensing when snoring is occurring; and electrically stimulating the at least one microstimulator implanted within the soft palate or the uvula in response to sensing snoring.

The present invention may further include a method wherein the microstimulator is implanted in a muscle selected from the group comprising: palatoglossus, palatopharyngeal, or musculus uvulae. The present invention may further include a method wherein the microstimulator is implanted proximate to a branch or terminal of the vagus X nerve. The method of the present invention may further implant a second microstimulator in the proximity of an anatomical structure selected from the group comprising: palatoglossus, palatopharyngeal, musculus uvulae, genioglossus, geniohyoid, levator palate, tensor palati, vagus X, hypoglossal, vagus pharyngeal branch, V3 branch trigeminal nerve.

The method of the present invention may further insert a distal tip of an insertion tool including a microstimulator through the oral mucosa of the soft palate; insert the distal tip of the insertion tool into the uvula; activate the insertion tool to deposit the microstimulator from the insertion tool; and remove the insertion tool from the uvula. The method of the present invention may further include positioning the microstimulator in or in the proximity of the musculus uvulae. The method of the present invention may further include positioning the microstimulator in the proximity of the terminal branches of the motor axons to the musculus uvulae, wherein the microstimulator includes a cathode and an anode; and positioning the microstimulator cathode in the proximity of the terminal branches of the motor axons to the musculus uvulae.

The method of the present invention may further comprise advancing a distal tip of an insertion tool through the oral mucosa to the soft palate to the uvula, wherein the distal tip of the insertion tool includes a microstimulator within a lumen of the distal tip; and testing microstimulator by emitting electrical stimulation from the microstimulator within the lumen of the distal tip; and withdrawing the insertion tool leaving the microstimulator within the uvula.

The invention may further include a method of implanting a microstimulator into the genioglossus muscle comprising inserting a distal tip of an insertion tool through the epidermis under the mandible; passing the distal tip of the insertion tool through the geniohyoid muscle; inserting the distal tip of the insertion tool into the genioglossus muscle; depositing the microstimulator in the genioglossus muscle; and e) removing the insertion tool from the uvula.

The method of implanting a microstimulator in the genioglossus may further include positioning the microstimulator in the proximity of the endplate zone of the radially oriented sagittal muscle fibers of the genioglossus muscle or the hypoglossal nerve, wherein the microstimulator includes a cathode and an anode; and positioning the microstimulator cathode in the proximity of the endplate zone of the radially oriented sagittal muscle fibers of the genioglossus muscle or the hypoglossal nerve.

The method of implanting a microstimulator in the genioglossus may further comprise advancing a distal tip of an insertion tool through the geniohyoid muscle to the genioglossus muscle, wherein the distal tip of the insertion tool includes a microstimulator within a lumen of the distal tip; and testing microstimulator by emitting electrical stimulation from the microstimulator within the lumen of the distal tip; and withdrawing the insertion tool leaving the microstimulator within the genioglossus.

The method of the current invention may include treating snoring in a patient comprising alternately stimulating at least a first and second muscle in the oropharynx to contract so that an airway passage remains substantially free of vibrating soft tissue during sleep. The present invention may further include a method for treating snoring in a patient comprising alternately stimulating at least a first and second muscle in the oropharynx to contract so that an airway passage remain substantially free of vibrating soft tissue during sleep, and selecting a pattern of stimulation such that while the first muscle is being contracted the second muscle may have a period of relaxation, and while the second muscle is being contracted, the first muscle may have a period of relaxation. The method of present invention may further include implanting at least a first microstimulator and a second microstimulator, and wherein the first and second microstimulators are alternately activated to cause the contraction of the at least first and second muscle in the oropharynx.

The present invention may further include a method for treating snoring wherein the first and second muscles are selected from the group comprising: palatoglossus, palatopharyngeal, musculus uvulae, genioglossus, geniohyoid, levator palati, tensor palati. The present invention may further include a method for treating snoring wherein the first and second muscles are selected from the groups of pairs comprising: tensor palati and palatoglossus; tensor palati and musculus uvulae; and geniohyoid and genioglossus.

The method of the present invention may further comprise applying electrical stimulations for a selected duration to stimulate at least the first muscle in the oropharynx to contract, and interrupting the electrical stimulation for a selected duration at a selected period to permit the first muscle in the oropharynx to relax.

It is an object of the invention to prevent or reduce the frequency or severity of snoring by causing at least one muscle to contract, producing force or motion to retract soft tissues of the oropharynx from the airway.

It is a further object of the invention to employ electrical stimulation of at least one nerve or muscle to achieve muscle contraction in the oropharynx.

It is yet another object of the invention to provide fully implanted microstimulators in or near at least one muscle or nerve to deliver electrical stimulation in the region of the oropharynx.

It is an additional object of the invention to provide wireless or leadless microstimulators that receive electrical power and/or control signals from a control unit located outside of the body.

It is an additional object of the invention to provide a microstimulator in a size and form that permits it to be injected into or near the muscles or nerves of the oropharynx.

In one embodiment, the invention uses miniature, single channel, wireless electrical stimulators injected into or near small muscles so as to selectively activate them to contract and prevent snoring.

A variety of anatomical structures in the oropharynx may contribute to snoring sounds and there are many separately innervated small muscles whose tone affects the position of these anatomical structures relative to the airway. It is therefore an object of the present invention to have a suitable methodology to identify the site where snoring originates in order to decide which nerve(s) and/or muscle(s) may be stimulated to reduce the frequency or severity of snoring. A flexible scope, such as a fiber optic scope may be used in one embodiment of the invention to identify the anatomical structure(s) involved in the generation of the snoring sounds and to determine the appropriate nerve(s) and/or muscle(s) and parameters of electrical stimulation required to reduce or eliminate the snoring.

Once a microstimulator has been implanted, there are stimulation parameters that may be selected for maximum effectiveness (e.g., pulse intensity, frequency, and on/off patterns). It is one object of the invention to monitor the oropharynx to determine the effects of selected stimulation and to direct the selection of an appropriate program of stimulation effective in reducing the frequency or magnitude of snoring.

DETAILED DESCRIPTION OF THE INVENTION

In one embodiment of the invention, at least one microstimulator 10 may be used to contract select muscles of the oropharynx 100 to decrease or eliminate the vibration of tissues along the airway passages 102 in patients who snore.

Figure 1:
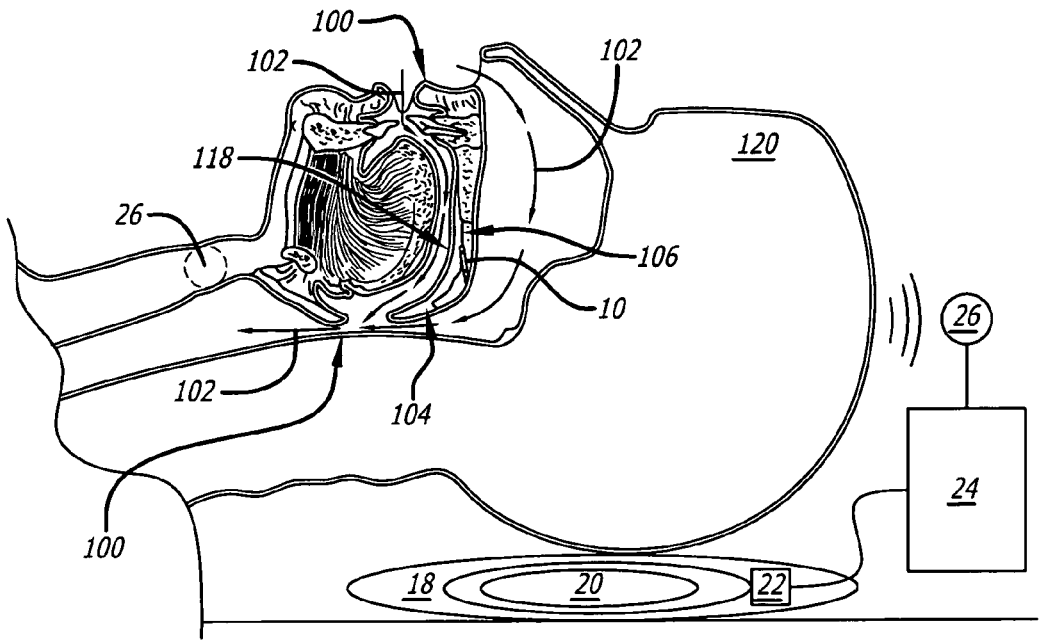
FIG. 1 is a schematic drawing depicting one position of a microstimulator and one method in which a microstimulator may be used to treat snoring.

Location of implantation. FIG. 1 is a schematic drawing depicting one position of a microstimulator 10 and one method in which a microstimulator may be used to treat snoring. In one embodiment of the invention, a microstimulator 10 may be implanted and activated so that it causes the contraction of at least one muscle in the oropharynx 100 creating force or motion to retract soft tissue from the airway passages 102. The oropharynx includes at least the oral cavity and pharynx, and anatomical structures therein. The airway passages 102 include the pathway that air travels between the mouth/nose and the lungs during inhalation and exhalation. More particularly the airway passages 102 are created by the inner lumen of the oral and nasal cavities, as well as the pharynx and trachea.

Figure 2:
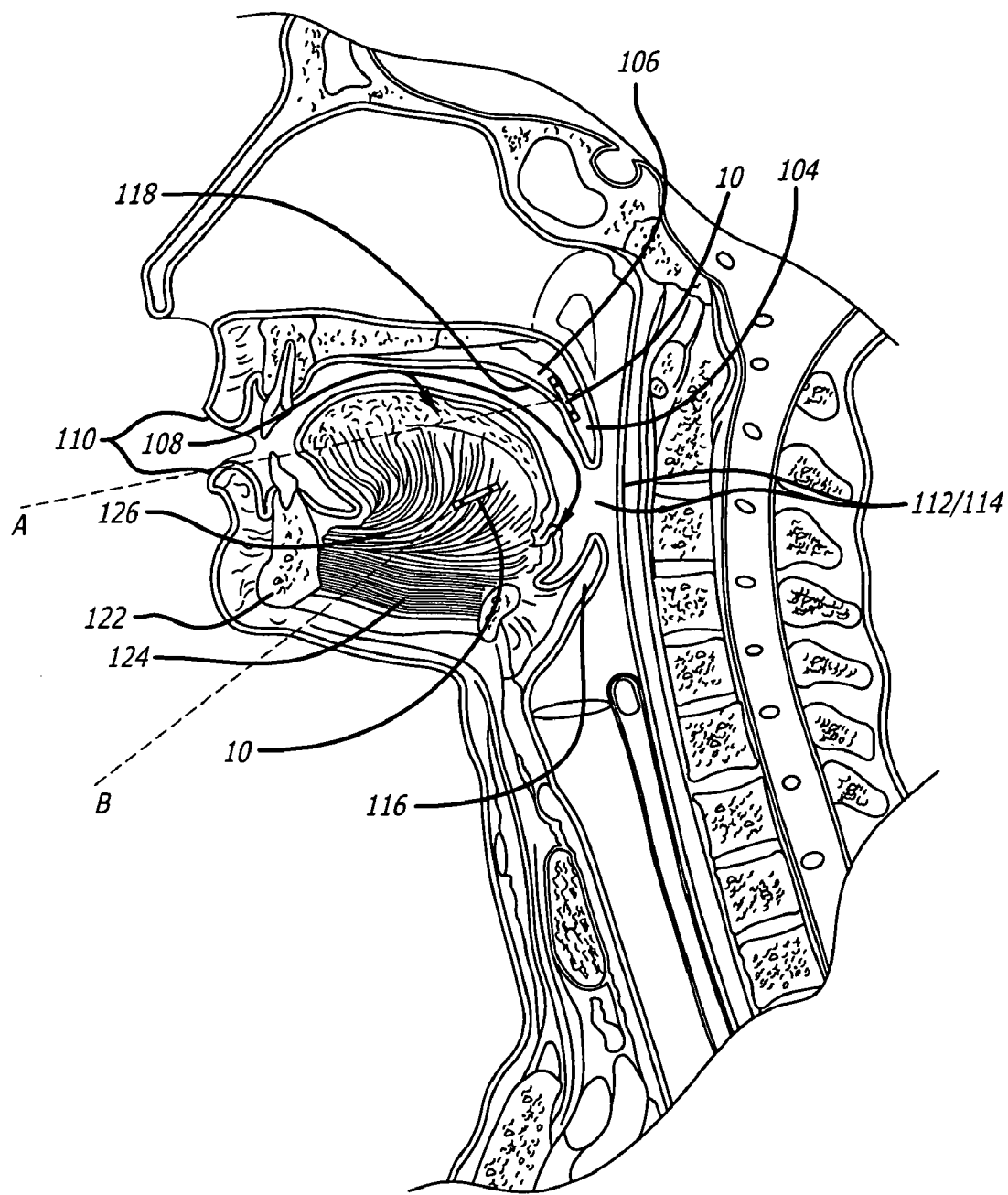
FIG. 2 is a sagittal view of the head demonstrating the location of a variety of anatomical structures implicated in snoring, as well as depicting at least two insertion approaches for the implantation of a microstimulator according to the present invention.
Figure 3A:
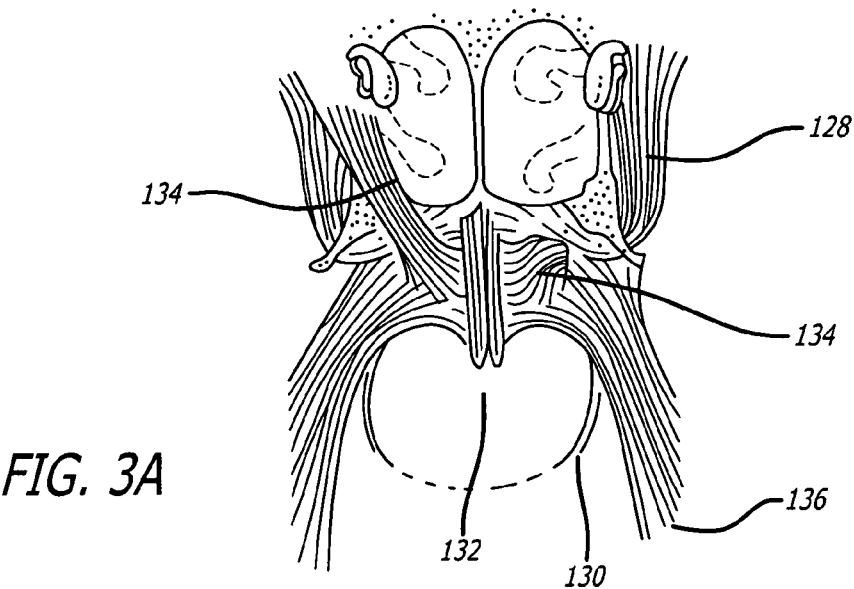
FIGS. 3A-D are schematic drawings depicting muscles near or in which microstimulators may be implanted to treat snoring; A) is a frontal view of muscles of the soft palate; B) is a cross-sectional view of the auditory tube and surrounding muscles; C) is a frontal view of the side walls of the pharynx; D) is a cross-sectional view of the pharynx.
Figure 3B:
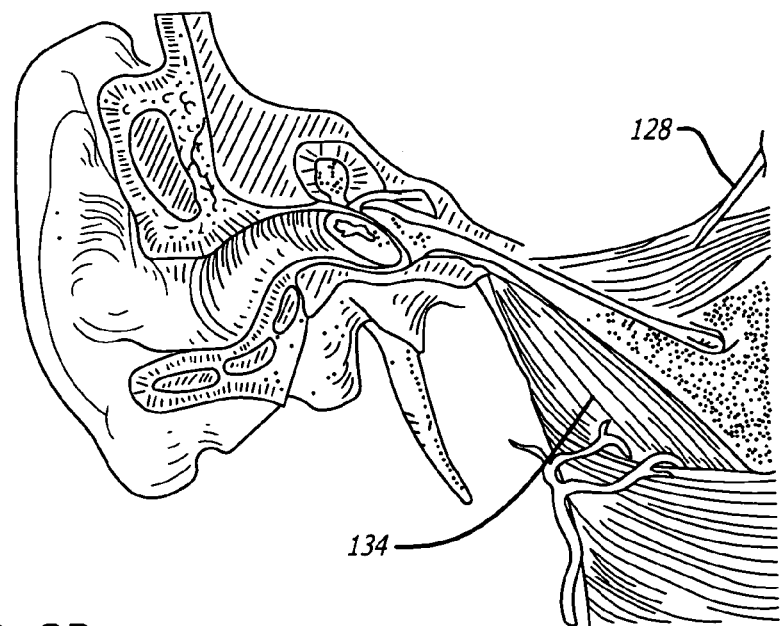
Figure 3C:
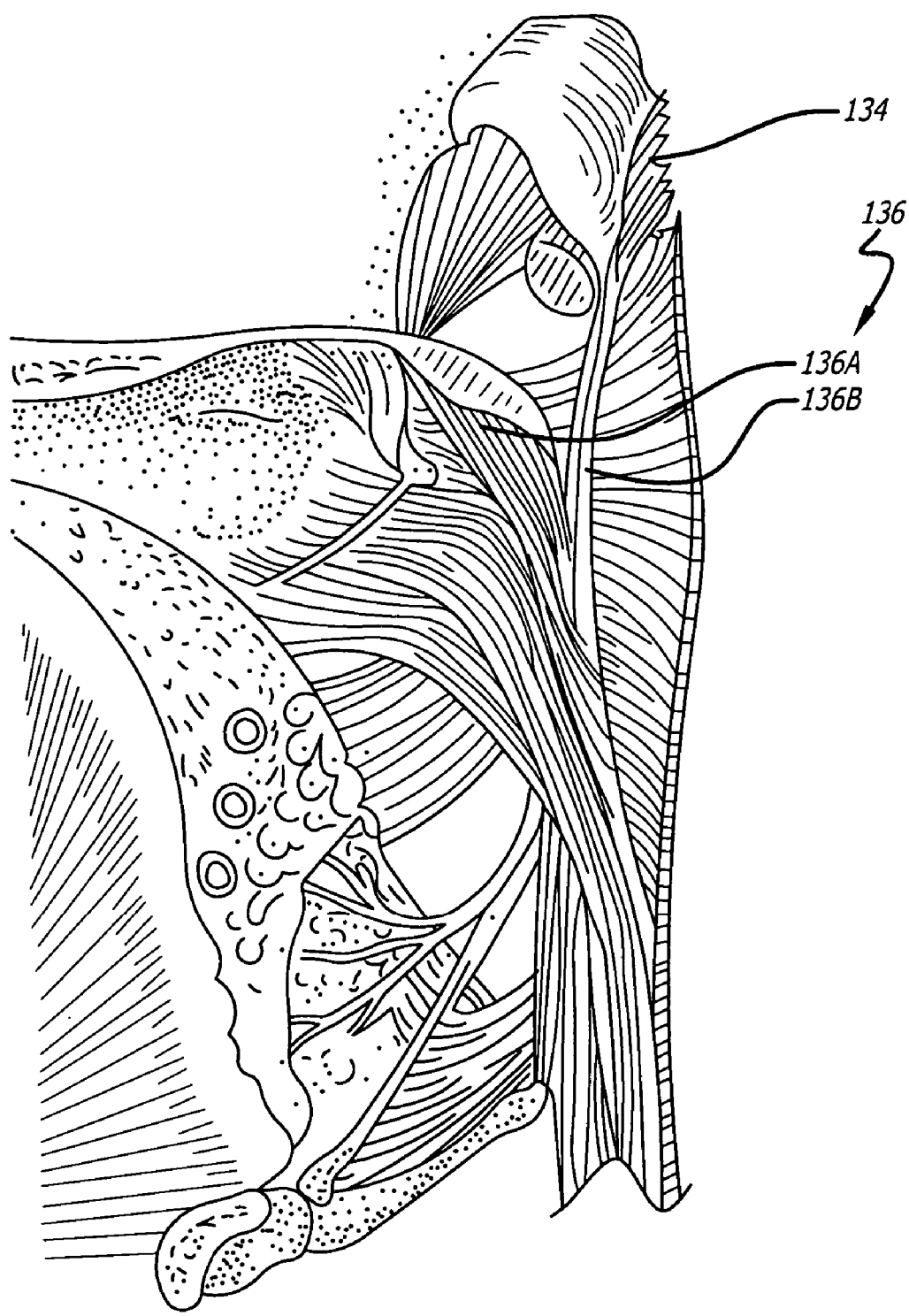
Figure 3D:
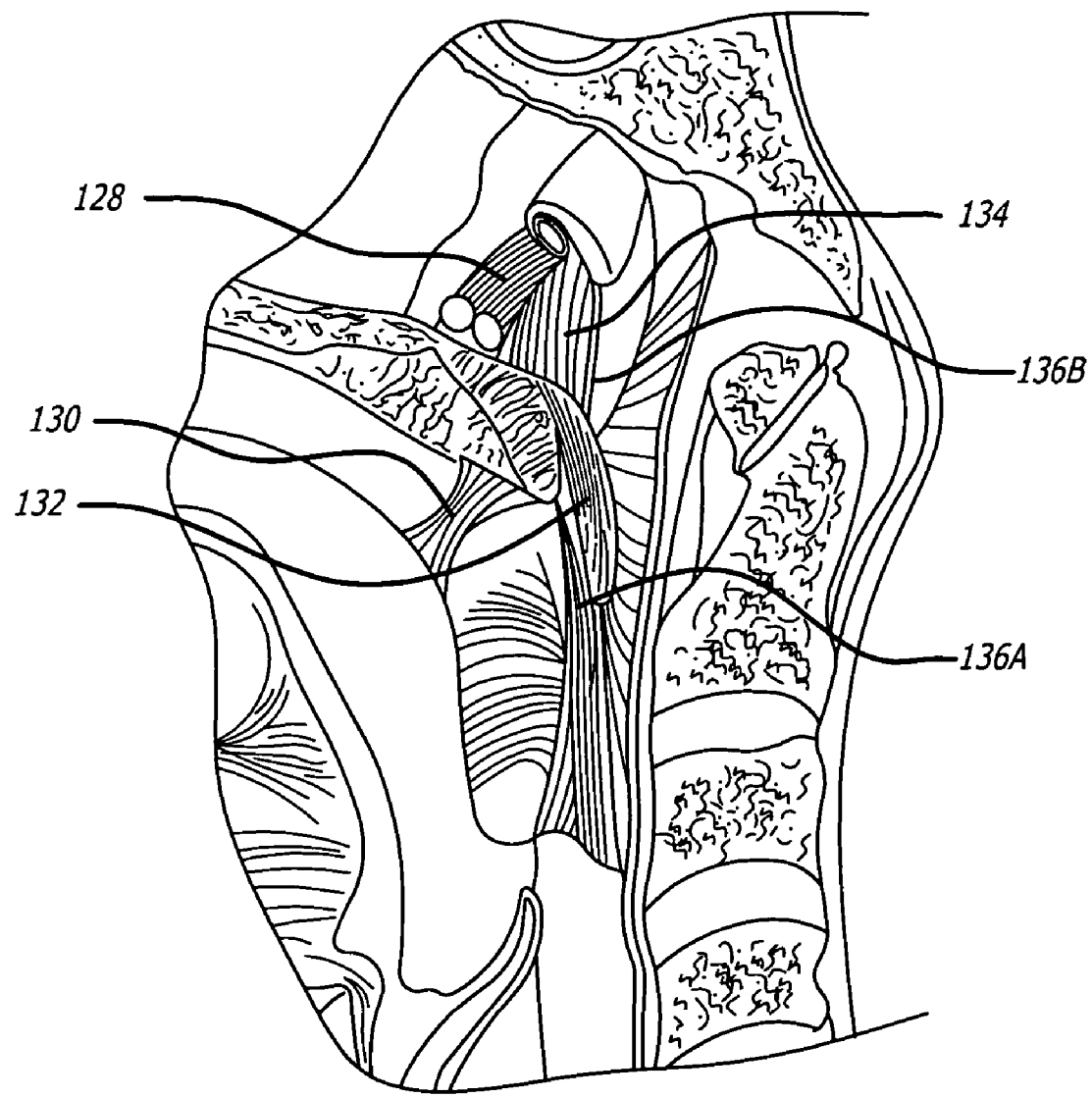

FIG. 2 is a sagittal view of the head demonstrating the location of a variety of anatomical structures implicated in snoring, as well as depicting at least two insertion approaches for the implantation of a microstimulator according to the present invention. The uvula 104, soft palate 106, tongue 108, lips 110 and posterior and lateral pharyngeal wall 112 and 114 and epiglottis 116 all may participate, although the uvula 104 soft palate 106 and are most commonly implicated in snoring.

In one embodiment of the invention, the at least one microstimulator 10 may be implanted in or near the uvula 104 or soft palate 106 as illustrated in FIG. 1. These anatomical sites contain muscle fibers that are innervated by motor neurons whose axons course through them. The axons of motor neurons may have a much lower threshold for electrical excitation than muscle fibers and each motor axon is connected to and may activate a large number of muscle fibers in the target muscle. In one embodiment of the invention, stimulation parameters may include a pulse width of 20-200 µs and a pulse current of 0.4-4.0 mA. Stimulation parameters may be varied depending on how close to the motor axons the microstimulator has been implanted. The intensity of an electrical stimulation pulse with these ranges of parameters is approximately related to the charge of the pulse, which is the product of pulse width and current (e.g., 1 mA×100 µs=100 nC).

The stimulation parameters may be selected such that the intensity of the pulse is effective in causing at least a muscle twitch. The stimulation parameter may be selected as the minimum effective intensity. This may be advantageous at least in that due to the small size of these anatomical sites and their coverage with mucosal tissue that contains sensory nerve fibers, it is advantageous to avoid producing sensations that might awaken the sleeping subject.

FIGS. 3A-D are schematic drawings depicting muscles near or in which microstimulators may be implanted to treat snoring; A) is a frontal view of muscles of the soft palate; B) is a cross-sectional view of the auditory tube and surrounding muscles; C) is a frontal view of the side walls of the pharynx; D) is a cross-sectional view of the pharynx.

If the vibrations associated with snoring appear to be associated with the uvula 104 and soft palate 106, one site of microstimulator implantation is in the distal soft palate 106 at the base of the uvula 104 near the musculus uvulae 132 (or uvular muscle; having an origin at the palatal aponeurosis and hard palate; insertion: soft tissue of uvula; innervation: unknown presumed branch of vagus; See FIGS. 6A-D) that elevates the uvula. This function is variable in some individuals. When they say "Ah," the uvula shrinks in length to less than one-half original size with pronounced horizontal ridges. In others, the uvular muscle does not seem to contract and all elevation appears to be due to action of levator palati. Implantation may also or alternatively be at or near palatal muscles, such as the palatoglossus 130 (having an origin at the palatal aponeurosis; insertion at the base of the tongue; innervation by the vagus X; See FIGS. 3A and D) which depresses soft palate; or the palatopharyngeus 136 having subparts including a: 1) palatopharyngeal portion 136a (having an origin at the palatal aponeurosis; insertion at the lamina of thyroid cartilage; innervation: vagus X; See FIGS. 3C and D) that depresses palate during inhalation with mouth closed and assists stylopharyngeus muscle in laryngeal elevation when swallowing; and 2) salpingopharyngeal portion 136b (having an origin at the posterior lamina of cartilaginous eustachian tube; insertion: fuses with palatopharyngeal portion to insert on thyroid lamina; innervation by the vagus X; See FIGS. 3C and D) presumed to assist in laryngeal elevation, but may also have a role in eustachian tube function. All of the above-noted muscles may both stiffen and change the shape of the upper airway. Both of these actions may be useful to reduce snoring, depending on the source of the vibrations producing the sound and the selection of the neuromuscular site or sites that are stimulated. Methods to identify which of these sites is most likely to be useful in a given subject are described below.

An alternative site of implantation may be at or near the branches or terminals of the vagus X nerve which innervates musculus uvulae 132, palatoglossus 130 and the palatopharyngeus 136.

As shown in FIG. 2, the implantation of a microstimulator near the uvula 104 or soft palate 106 may be accomplished by anesthetizing the soft palate mucosal surface 118 and passing an insertion tool 36 into the base of the uvula 104 along the line A indicated by the arrow in FIG. 2 that points to the musculus uvulae 132. The microstimulator may be positioned such that the cathodal stimulating electrode 14 or 16 may be positioned near the terminal branches of the motor axons to the musculus uvulae 132 and/or palatoglossus 130 and the palatopharyngeus 136, respectively.

Stimulating these motor axons causes the muscle fibers that they innervate to contract. The effect is to withdraw the uvula 104 and or soft palate 106 from the respiratory airflow 102 and/or stiffen the distal soft palate 106, hence reducing or eliminating vibration.

If the vibrations are associated with the tongue 108, the microstimulator 10 may be implanted in the posterior portion of the tongue 108 in the sagittal plane. As shown in FIG. 2, this implantation can be accomplished by passing an insertion tool 36 from under the mandible 122, through the geniohyoid muscle 124 and into the genioglossus muscle 126, along the line B indicated by the arrow in FIG. 2 that points to the genioglossus muscle 126. The microstimulator's 10 cathodal stimulating electrode 14 or 16 may be located close to the endplate zone of the radially oriented sagittal muscle fibers.

The resulting protrusion of the tongue lifts it away from the soft tissues of the posterior and lateral pharynx 112/114, opening the airway passages 102. The approach of injecting the microstimulator via this route (as opposed to into the tongue through the mucosal surface) may be advantageous at least in that 1) it is easier to anesthetize the entry point for the insertion tool, 2) easier to stay on midline to target tongue protrusor motor units and avoid injury to nerves and blood vessels, easier to observe the effects of test stimului on the tongue motion before releasing a microstimulator in situ, less chance of contaminating the insertion tool and microstimulator with bacteria from the oral cavity. The muscle fibers of the tongue are organized into functionally and anatomically distinct groups based on their position and orientation within the tongue. The posteriorly directed portion of the parasagittal fan of muscle fibers originates from the mandible and produces tongue protrusion. Endplate bands innervate the midpoints of these fibers and extend to the midline. Therefore, a microstimulator may be placed in the in the midplate near the endplates to produce symmetrical protrusion of the tongue.

In one embodiment, the microstimulator may be implanted in the proximity of the hypoglossal nerve. The hypoglossal nerve branches to the genioglossus 126 and enters the tongue inferolaterally, longitudinally and radially in order to innervate various of the functionally distinct groups of muscle fibers in the tongue. It is difficult to predict the net motion that will result from stimulation of the hypoglossal nerve because it depends on the relative activation of these functionally distinct groups. Nevertheless, any activation of the muscle fibers will increase the mechanical stiffness of the tongue, reducing its tendency to vibrate as air passes by it.

If the vibrations are associated with the posterior and/or lateral pharyngeal walls 112/114, then stimulation of the genioglossus muscle 126 may be effective, even though the resulting muscle contractions do not directly effect the tissues of the posterior and lateral pharynx 112/114 whose vibrations are the source of the snoring. Rather, protrusion of the tongue generally increases the cross-sectional area of the airway passages 102, reducing the local velocity of airflow, in turn reducing the tendency of the adjacent tissues to vibrate and produce turbulence and snoring.

The microstimulator 10 may be implanted in the geniohyoid muscle 124 itself, whose action tends to increase the diameter of the oropharyngeal airway passages 102. If this is desired, then the microstimulator can be implanted along line B of FIG. 2, but more superficially in the geniohyoid muscle 124 itself.

Further, a microstimulator 10 could be positioned so that one each of its two electrodes 14/16 lies within one each of the geniohyoid 124 and genioglossus muscle 126, respectively. In this embodiment, it may be possible to stimulate both muscles simultaneously with sufficiently strong stimulation pulses.

Snoring originating from the epiglottis 116 tends to be associated with respiratory sounds in young infants in which the epiglottis has not yet developed sufficient stiffness in its cartilage. This cause of snoring usually resolves spontaneously. However, if snoring persists through development, a microstimulator may be implanted in any muscle or adjacent to any nerve innervating a muscle whose contraction may move the epiglottis out of the airway during sleep. The position of the microstimulator relative to the epiglottis should be carefully selected so as to not interfere with the normal functioning of the swallowing reflex.

Applicants have also found that snoring in at least some patients may result from inappropriate action of the palate elevator muscles during sleep that shifts the uvula 104 and soft palate 106 actively, but briefly, into the airway passages 102. For example, levator palati 134 (or levator veli palatine; having an origin at the apex of the petrous bone descending to the palate along the floor of the eustachian tube; insertion at palatal aponeurosis; innervation: pharyngeal branch of vagus nerve X; See FIGS. 3A-D) elevates the soft palate 106, such as when a patient says, "Ah!". Also, the tensor palati 128 (or tensor palatini, tensor veli palatine; having an origin at the scaphoid fossa of sphenoid bone an area lateral to base of medial pterygoid plate; insertion: muscle fibers descend vertically form a tendon which wraps around hamulus bone then insert about horizontally onto palatal aponeurosis; innervation by the trigeminal nerve V (V3 branch); See FIGS. 3A-D) tenses the palate. Microstimulator implantation in or near the levator palati 134 and/or tensor palati 128 is expected to be effective in overcoming motion that shifts the uvula 104 and soft palate 106 into the airway passages 102. This finding emphasizes the importance of direct visualization of the oropharynx to identify correctly the site and cause of snoring and to adjust the stimulation parameters of the implanted microstimulator(s) to counteract it effectively.

As above, the microstimulator may be implanted in the proximity of the branch or terminals that innervate the levator palati 134 or the tensor palati 128, including the pharyngeal branch of vagus nerve or the trigeminal nerve V (V3 branch), respectively.

For all implantation sites, the position of the microstimulator 10 with respect to both the neuromuscular targets and the sensory innervation of the oropharynx should be considered. If the microstimulator 10 tends to activate sensory nerves at lower stimulus thresholds than those for the desired neuromuscular activation, the patient will experience disagreeable sensations that are likely to interfere with sleep. The microstimulator 10 and the insertion tool 36 used to implant them may therefore be selected to have: 1) a small size relative to the implantation site; 2) permit orientation specific placement relative to the implantation site; 3) permit application of test stimulation pulses during the implantation process and 4) allow the minimum effective stimulation parameters to be determined.

For all implantation sites, the microstimulator implant may be oriented more or less vertically when the patient sleeps in the supine posture. This positioning facilitates transmission of power and/or command signals to the microstimulator 10 from an external controller 24, including components such as a transmission coil 20 located in the pillow 18 under the head, as illustrated in the cross-section in FIGS. 1 and 4. In this orientation, the axes of the transmission coil 20 and a receiving coil located inside the microstimulator electronic subassembly 12 may be aligned coaxially, which increases the coupling coefficient between them.

When the microstimulator 10 is implanted within a muscle, it may be positioned within the belly of the muscle in which contraction is desired. This may be advantageous at least in: 1) permitting the selective activation of the desired muscle; 2) reducing inadvertent excitation of other, nearby nerves and muscles and 3) reducing migration after implantation to an inappropriate location or position.

Plurality of microstimulators. The number and location of microstimulators 10 implanted may depend on the nature of the underlying pathophysiology of the snoring, as discussed. In one embodiment, the size of the microstimulator is selected so that they are small enough that at least two can be placed at different locations within the same muscle, where they will recruit largely non-overlapping populations of motor units. In one embodiment, the microstimulators are individually addressable and/or can be separately commanded to produce a desired pattern of stimulation pulses to achieve relief from snoring.

A plurality of microstimulators may be implanted in the oropharynx, such as one in each of any of positions described. By way of example, one microstimulator may be implanted in each of the geniohyoid 124 and genioglossus muscles 126. By way of further example, one microstimulator may be implanted in each of the tensor palati 128 and palatoglossus 130 muscles. By way of further example, one microstimulator may be implanted in each of the tensor palati 128 and musculus uvulae 132 or in other combinations involving other sites as identified above. A microstimulator may also be placed at or near the oropharynx generally to serve a detection function, described below.

Those skilled in the art and familiar with the neuromuscular anatomy of the upper airway passages 102 would understand that implanting microstimulators at locations other than the ones depicted in the figures may aid in the treatment of snoring.

Microstimulators. In order to treat snoring by the methods taught in this invention, implanted devices may be used that are small enough to inject into the subject through a hypodermic needle, that require no physical connection to a source of power or command signals, and that can be controlled to produce stimulation pulses whose strength and timing can be adjusted to meet the needs of the subject. The function, form and detailed design of microstimulators that may be useful in this invention have been described in detail in U.S. Pat. Nos. 5,193,539, 5,193,540, 5,312,439, 5,324,316, 5,405,367, 6,051,017, 6,175,764, 6,181,965, 6,185,455, 6,214,032, 6,240,316, the contents of which are incorporated herein by reference.

The microstimulator 10 for use in the present invention may be a wireless miniature device that can be implanted in or near a target muscle or nerve without requiring leads for electrodes, power or command signals. For example, a BION® (BIONic Neuron, Advanced Bionics Corp., Valencia, Calif.) may be used as a microstimulator in this invention. BIONs® are single channel, wireless (leadless) microstimulators (about 16 mm long×2 mm in diameter) that can be injected in or near muscles or nerves. Each microstimulator may receive power and digital command data via an external controller 24 including an RF transmission coil 20 to produce stimulation pulses with a selected intensity and pattern. Each microstimulator may receive the RF energy and convert it into an AC or DC supply to operate an integrated circuit chip, and store pulse energy in a capacitor. The microstimulator may receive command data, and generate a stimulation pulse releasing energy stored in a capacitor, then recharge a capacitor between output pulses.

Figure 5A:
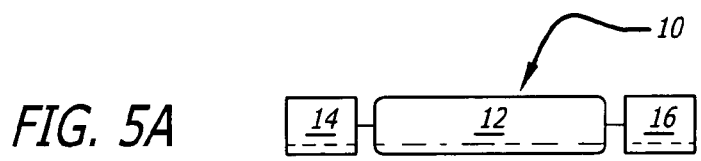
FIG. 5A is a schematic drawing depicting one embodiment of a microstimulator which may be useful in the invention.

FIG. 5A is a schematic drawing depicting one embodiment of a microstimulator 10 which may be useful in the invention. The size of the microstimulator 10 may be selected so as to minimize tissue damage at the selected site of implantation, minimize discomfort, minimize normal activity of the muscle/nerve in or near which the microstimulator is implanted. As shown in FIG. 5A, each microstimulator 10 may consist of three elements: electronic subassembly 12 and at least two electrodes 14 and 16 (e.g., one anode and one cathode for the application of stimulation current to surrounding tissue). The microstimulator electronic subassembly 12 may include a power source and/or control system for regulating parameters of electrical stimulation. Alternatively, the power source and/or control system may reside outside of the microstimulator 10, and even outside of the body in the controller 24.

FIG. 1 is a schematic drawing depicting one position of a microstimulator 10 and one method in which a microstimulator 10 may be used to treat snoring. For example, in one embodiment, the microstimulator 10 may include an electronic subassembly 12 which may receive power and/or command signals by inductive coupling from an external controller 24, including an antenna/transmission coil 20 located outside the body. The electronic subassembly 12 may also store electrical power within the microstimulator. In some embodiments, the transmission coil 20 may be housed within a structure 18, such as a pillow which may be positioned in a suitable location, such as under the patient's head 120 to guarantee physical proximity to the implanted microstimulator 10. The transmission coil 20 may be energized with a radio frequency electrical current generated by a driver 22 and modulated according to a stimulation parameters that have been loaded into a digital memory contained within a controller 24.

Battery operated. In another embodiment, a miniature power storage component may be incorporated into each microstimulator 10, such as a miniature rechargeable lithium cell, plus electronic means to store and execute stimulus parameters and the desired temporal pattern of successive stimulus pulses, such as an electronically erasable and programmable read-only memory. This approach is well-described in the prior art, such as U.S. Pat. Nos. 6,185,452 and 6,240,316, the content of which is incorporated herein by reference. Such internally powered microstimulators 10 may be capable of autonomous generation of the temporal pattern of stimulation treatment even if the microstimulator 10 is not proximate to a transmission coil 20, for example. Because the storage capacity of a miniature power storage component within the microstimulator 10 may be limited, the microstimulator 10 may also use power transmitted from transmission coil 20 whenever available to reduce demand on the power storage component and to recharge it back to its capacity. Transmission coil 20 or another command and/or power transmission device can be used to command microstimulators 10 to begin or cease such autonomous operation, such as when the patient goes to bed or arises or begins snoring.

The stimulation parameters may constitute a string of command signals. Each command signal may contain digital data identifying the address of a selected microstimulator 10 that is to generate selected electrical stimulation pulses, the pulse intensity, frequency and on/off duty cycle patterns required to evoke the desired muscle contraction. Stimulation parameters may include parameters will generally lie in the ranges including but not limited to about 10-1000 nC, about 1-30 pps, and about 20-100% duty cycle.

The microstimulator 10 may be modular design in design and individually and discretely addressable since this design would permit additional channels of stimulation to be added to the patient at any time without interfering with those channels installed previously.

In one embodiment, the microstimulator may provide electrical stimulation to muscles of the oropharynx only when snoring is detected. For example, as shown in FIG. 1, a detector 26, such as a microphone, may be placed near the patient; detect the sounds of snoring; and convey them to controller 24 to act as a trigger signal. An acoustic signal processing algorithm in controller 24 may determine if the detected sounds are actually snoring (as opposed to other ambient sounds) and may initiate a predetermined pattern of stimulation consisting of one or more cycles similar to that described above.

In one embodiment, a microstimulator 10 may be used as a sensor 26 function. For example, a microstimulator may be used to detect vibrations of the oropharynx during sleep, detect volume, or the tone of the muscle in which it is implanted. Such vibrations could be detected by a microminiature accelerometer fabricated according to MEMS (Micro Electro Mechanical Systems) technology, which is well-known in the art, examples of which are described in "Highly Symmetric Tri-axis Piezoelectric Bimorph Accelerometer," by Qiang Zou, Wei Tan, Eun Sok Kim and Gerald E. Loeb, to be published in 17*th IEEE Conference on Micro Electro Mechanical Systems* (MEMS 2004), IEEE, 2004 (4 pp.), and incorporated herein by reference. The data may be used by the same microstimulator 10 to initiate an electrical stimulation. The data may be telemetered on a carrier frequency directly to another microstimulator 10 to cause an electrical stimulation. The data may be telemetered to a receiving coil 20. The detection data may be conveyed to a controller 24, which utilizes the information to decide what and when stimulation is required to alleviate the snoring. One means of transmitting data from one microstimulator 10 to receivers of such data is by "suspended carrier transmission" as described in U.S. Pat. No. 5,697,076 and incorporated herein in reference.

Implantation by Injection Device. The microstimulators 10 may be of a size and shape to be implantable by injection. Injection of a microstimulator may be by insertion at the selected anatomical site for example, through the lumen of an insertion tool 36, such as a flexible tube, a rigid hypodermic needle or a laparoscopy tool. An insertion tool 36 and method of implantation of a microstimulator may be used such as described in "Cargo Delivery Capsule" U.S. Provisional Patent Application No. 60/476,007 filed Jun. 4, 2003 or "Injection Devices and Methods for Testing Implants Prior to Positioning" U.S. Utility application Ser. Nos. 10/461,560 or 10/461,132 filed Jun. 12, 2003.

The insertion tool 36 used in the implantation of a microstimulator may be selected to permit site-specific and orientation specific placement of the microstimulator 10 at the selected anatomical location. Further, the insertion tool 36 may be designed to permit the testing and/or repositioning of a microstimulator 10 at the selected anatomical location prior to release from the insertion tool 36. The insertion tool 36 may be designed to minimize damage to the microstimulator 10, as well as minimize tissue damage, risk of infection and patient discomfort during the implantation procedure.

Figure 5B:
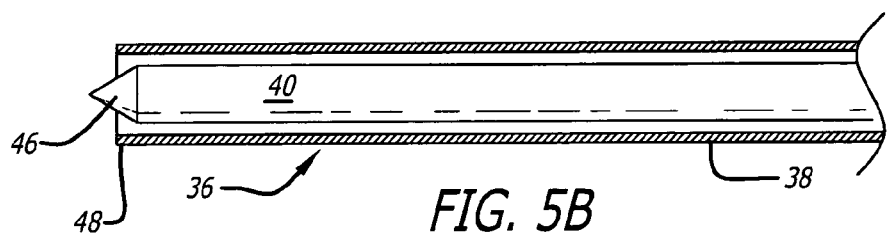
FIG. 5B depicts one embodiment of an injection device which may be useful in the present invention.
Figure 5C:
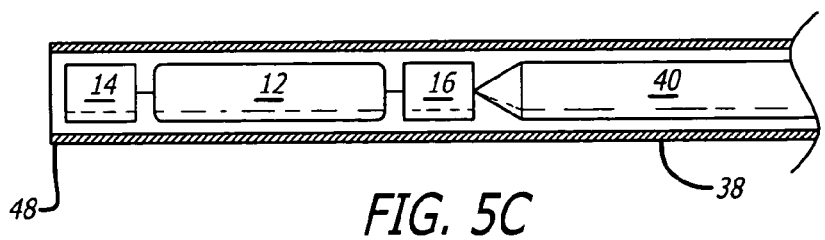
FIG. 5C depicts one method of using an injection device to implant a microstimulator.

FIG. 5B depicts one embodiment of an insertion tool 36 which may be useful in the present invention. The insertion tool 36 may include a plastic sheath 38 around a removable metal trochar 40. Trial electrical pulses can be applied through the trochar 40 to identify the desired target for implantation. The trochar 40 may then be removed from the sheath 38 and the microstimulator 10 injected through the distal most tip of the sheath 38 into the site. FIG. 5C depicts one method of using an injection device to implant a microstimulator.

Methods of use. The best anatomical site(s) for implantation of microstimulators and the parameters of stimulation to alleviate snoring may be difficult to determine in a given patient.

Figure 4:
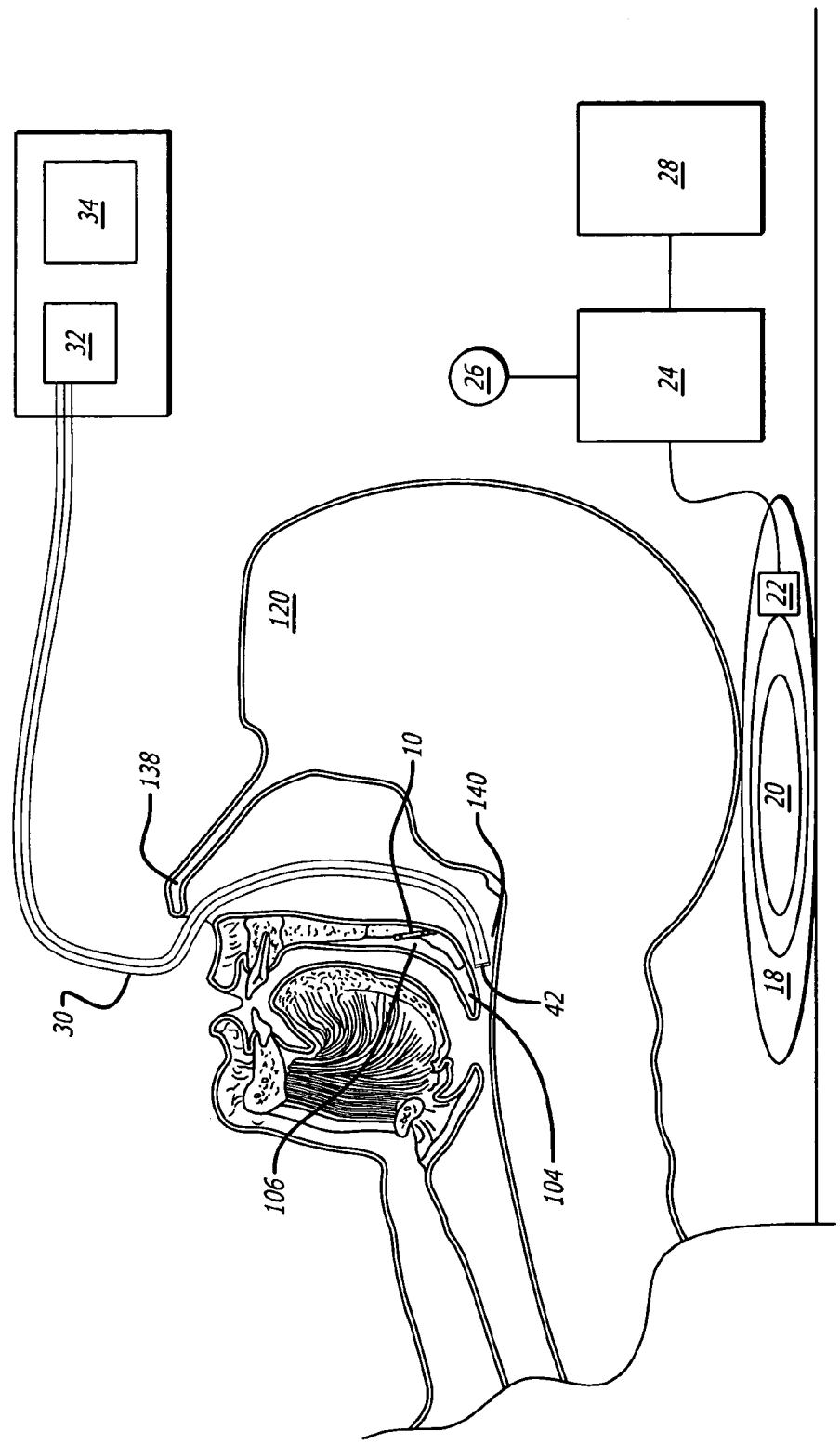
FIG. 4 is a schematic drawing depicting one method in which a subject may be monitored to evaluate the selection of an anatomical location, implantation of a microstimulator and modification of parameters of electrical stimulation to treat snoring.

Monitor patient to determine soft tissue vibrating during snoring. As illustrated in FIG. 4, a scope 30 can be placed through the nose 138 into the back of the nasopharynx 140 where it can be used to visualize anatomical structures in the oropharynx 100 and airway passages 102 while a patient is sleeping and snoring. The scope 30 and related equipment 32 and 34 may be used for remotely steering the scope tip 42 and displaying video images acquired from its tip 42. In one embodiment, the scope 30 may be made of a thin and flexible fiber optic cable such as those used in pediatric endoscopes. The scope 30 may be inserted through the patient's nose 138 so that it lies in the back of the upper airway passage 102 where it can be steered so as to visualize the various soft tissues of the oropharynx 100 that are likely to be responsible for snoring. When the patient is asleep and snoring occurs, the clinician can use the scope 30 to visualize the location of the vibrating tissue that gives rise to the snoring sounds. This information may provide guidance in selecting the sites to be implanted with a microstimulator 10.

In one embodiment, the efficacy of an anatomical site selected may be tested prior to the implantation of a microstimulator 10. For example, stimulation pulses may be applied to a potential anatomical site through conventional electrodes that can be incorporated into or passed temporarily through an insertion tool 36. Ultrasonic imaging of an insertion tool 36, microstimulator 10 and the oropharynx 100 may be used during the implantation procedure.

In one embodiment, the function of the microstimulator 10 may be tested at the implantation site prior to release from the insertion tool 36. For example, where the insertion tool 36 includes a sheath 38, the microstimulator 10 may be advanced to the distal-most end of the sheath and stimulated to produce an electrical stimulation. If the desired response is obtained, the sheath 38 may be retracted holding the microstimulator 10 in position with a trochar 40. Finally, the trochar 40 may be withdrawn from the implantation site.

In one example, the microstimulator stimulation parameters can be selected by variously activating the implanted microstimulator(s) 10, for example via a transmission coil 20 and monitoring the stiffness of the overlying tissue or breathing and snoring of a sleeping patient, such as by measuring vibrations in the oropharynx, volume of sounds in the proximity of the oropharynx, or the activity or tension in a muscle in the oropharynx. The activation of a microstimulator 10 and control of the stimulation parameters may be performed by a user interface such as is provided by application-specific software running on a personal computer 28 that may be functionally connected to a controller 24, as illustrated in FIG. 3.

After implantation of at least one microstimulator 10, monitoring may continue, such as via a scope 30, to observe the muscle contraction produced by transmitting command signals for various patterns of electrical stimulation to the microstimulator 10. This procedure may be conducted before the microstimulator 10 is released from the insertion tool. This procedure may also done while the patient sleeps.

The clinician may use software in a computer 28 to devise various stimulation parameters and to deliver them to controller 24, which may formats command signals for transmission to the implanted microstimulator 10, such as via transmission coil 20 and driver 22. When a stimulation parameter program has been identified that is effective in contracting at least one muscle in the oropharynx 100 to stiffen the proximate tissue or retract soft tissue from the airway passages 102, it may be loaded into non-volatile memory in controller 24 so that the patient can use the controller 24 to deliver the stimulation program at home while sleeping, as illustrated in FIG. 1, described above. In one embodiment, controller 24 may be turned on and running a stimulation program such that command signals are sent to at least one implanted microstimulator 10 when and only when the patient places their head 120 in the proximity of a transmission coil 20, thereby entering the magnetic field generated by transmission coil 20 and driver 22.

In some embodiments, the microstimulator 10 may only receive power and/or command signals if it is sufficiently close to the RF transmission coil 20. Therefore, it is possible for the treatment to fail if during sleep the patient moves their head away or turns to an orientation for which the coupling between microstimulator 10 and transmission coil 20 is too weak for normal operation. Various technical approaches can be employed to address this problem.

In one embodiment, the transmission coil 20 may be adapted so as to be attached to the patient during sleep, such as in the form of a collar or clip to be attached to the patient's clothing in the proximity of the microstimulator.

In one embodiment, a back-telemetry signal may be generated from each microstimulator 10 to a transmission coil 20, which then acts as an antenna to detect this back-telemetry signal. Various means for generating such back-telemetry signals are well-known in the field of implantable transponders for use in the identification of animals, such as those described in U.S. Pat. Nos. 5,211,129 and 5,697,076, the content of which are incorporated herein by reference. For example, if and when a microstimulator 10 receives a command signal, it may generate both the requested stimulation pulse and a back-telemetry signal which is then received by transmission coil 20 and processed through its supporting driver 22 and conveyed to controller 24. If controller 24 determines that an unacceptable number of the stimulation commands that it issues are not received by and acted upon by a microstimulator 10, then the controller 24 may generate an audible or visible alarm designed to alert the patient to reposition themselves relative to the transmission coil 20 so as to receive the prescribed treatment.

In one embodiment, the system may also include the transmission of an acknowledgement signal from the microstimulator 10 to a controller 24, where the acknowledgement signal indicates that the microstimulator has received a control signal from a controller. This embodiment may be useful at least in that it may be difficult for a patient to sense whether or not a microstimulator is active because the muscles which are stimulated are small and produce mechanical actions that are not readily felt or visible.

In one embodiment, the invention may allow a clinician to specify the stimulation program. The system may also include transmitting an acknowledgement signal from the microstimulator to a controller, wherein the acknowledgement signal indicates that the microstimulator has received a control signal from a controller. The stimulation program may include alarm conditions and contingencies specified by the clinician. The system may also allow tracking/recording and responding back to an alarm system events as part of the program usage and control. The system may also provide to the patient acknowledgement confirming when the microstimulator 10 is correctly positioned relative to external components of the system and/or the system is working correctly (such as immediate feedback). The system may also notify the patient if failures over certain clinician set criteria occur (e.g., snoring persists in spite of implantation and stimulation of microstimulators according to the set parameters.) Finally, the system may include a mechanism to start and stop alarm conditions that arise during sleep. The mechanism may be selected to be intuitive to the patient and easy to operate so that it can be silenced quickly and easily upon waking from sleep.

Stimulation Parameters. The stimulation patterns are preferably selected to activate the selected microstimulator 10 at the selected time, at the selected intensity for the selected duration of time to cause contraction of at least one muscle in the oropharynx. The stimulation parameters may be selected to cause contraction of a muscle, but also not fatigue the muscle. Ultimately, muscle fatigue leads to a flaccid muscle, loosening of tissue proximate to the muscle and the retreat of the soft tissues into the airway passages 102 of the patient and snoring may resume. The stimulation parameters may be selected so as to cause the desired change in the tone of the airway passages 102, while minimizing unwanted motion, patient arousal during sleep, cutaneous stimulation, interference with normal movement of the muscle or function of the nerve.

The stimulation parameters may be loaded into a controller 24 which is positioned to control the microstimulator 10, or may be loaded directly into the microstimulator 10.

The electrical activation of the microstimulator 10 to contract a muscle in the oropharynx need not be synchronized with either inhalation or exhalation. However, a reduction in the frequency or magnitude of snoring may be obtained while at least some stimulation of the oropharyngeal muscle(s) is present. Continuous stimulation at one site however, may be undesirable because the activated muscle fibers may fatigue quickly, particularly if the hydrostatic pressure in the muscle resulting from the contraction reduces blood flow to the local muscle fibers. Thus, it is preferable alternately to apply stimulation to contract the muscle, then allow a period for the muscle to relax, rather than contracting a muscle continuously.

In one mode of operation, an electrical stimulation pattern may be applied less than continuously to at least one microstimulator to intersperse periods of no stimulation to reduce muscle fatigue. The muscles and soft tissues of the airway passages 102 have inertia and viscoelastic properties that slows their rate of relaxation. Fatigue tends to occur rapidly when muscles contract continuously for more than a few seconds because contraction is accompanied by an increase in hydrostatic pressure that may be sufficient to occlude blood flow in the muscle. Brief interruptions of stimulation may be sufficient to reduce hydrostatic pressure so as to permit circulation of the blood but not so long as to allow the soft tissues to relax into a position where snoring recurs. In one embodiment stimulation parameters may include interruptions in the stimulation pattern in the range of about 0.2-2 s every about 5-20 s.

Plurality of microstimulators. If the soft tissues responsible for the snoring retreat into the airway passages 102 and begin vibrating upon relaxation of the muscle, more than one microstimulator may be implanted within the same muscle (where they will recruit largely non-overlapping populations of motor units) or in different muscles. A plurality of microstimulators may be separately stimulated in an alternating pattern, so that each muscle has a period of rest but at least one is always being stimulated.

Although now having described certain embodiments of a method for treating snoring, it is to be understood that the concepts implicit in these embodiments may be used in other embodiments as well. In short, the protection of this application is limited solely to the claims that now follow.

We claim:
1. A method of treating snoring comprising:
 a) inserting an imaging device into the airway passage of a patient;
 b) monitoring, with the imaging device, the airway passage during sleep to identify at least one anatomical structure in the airway passage that vibrates during snoring;
 c) introducing, with an injection tool, at least one microstimulator in the proximity of the at least one anatomical structure identified in step b), wherein the injection tool penetrates tissue in the proximity of the identified anatomical structure;
 d) energizing the microstimulator to deliver a test electrical stimulation to the anatomical structure to cause at least one muscle to contract and reduce the vibration of the anatomical structure, wherein the microstimulator is energized while held within the lumen of the injection tool;
 e) observing, with the imaging device, whether the test stimulation causes a decrease in vibration of the anatomical structure; and f) releasing, if a decrease in vibration of the anatomical structure is observed, the microstimulator from the injection device into the anatomical structure.

2. The method of claim 1, wherein the inserting further comprises inserting a distal end of a scope such that the distal end is located in the upper airway of the patient and monitoring the airway passage during sleep.

3. The method of claim 1, wherein the releasing comprises activating the injection tool to eject the microstimulator from the injection tool, and removing the injection tool from the anatomical structure.

4. The method of claim 1, further comprising testing the microstimulator by emitting electrical stimulations at a plurality of intensities, and observing the anatomical structure to determine the intensity which decreases the vibration of the anatomical structure.

5. The method of claim 4, wherein the plurality of intensities are selected from a range of about 8 to about 800 nC.

6. The method of claim 1, further comprising energizing the microstimulator at a selected frequency to deliver an electrical stimulation to the anatomical structure to cause at least one muscle to contract and reduce the vibrations of the airway passage.

7. The method of claim 6, wherein the selected frequency is within a range of about 1 to about 30 pulses per second.

8. The method of claim 6, further comprising providing interruptions of a selected duration and period in the electrical stimulation to permit the at least one muscle to relax.

9. The method of claim 8 wherein the duration of the interruption is within a range of about 0.2 to about 2 seconds, and the selected period is from a range of about 5 to about 20 seconds.

10. The method of claim 1, further comprising:
a) sensing when snoring is occurring; and
b) generating an electrical stimulus from the microstimulator to contract an oropharyngeal muscle, in response to sensing snoring in step a).

11. The method of claim 10, wherein snoring is sensed by detecting mechanical vibrations of at least one anatomical structure.

12. The method of claim 10, wherein snoring is sensed by acoustically detecting sounds generated by vibrating at least one anatomical structure in the airway passages.

13. The method of claim 1, wherein the energizing includes delivering a control signal to a pair of electrodes of the microstimulator.

14. The method of claim 1, wherein the anatomical structure is selected from the group comprising: the soft palate or the uvula.

15. The method of claim 14, wherein the microstimulator includes an electrical circuit configured to generate an electrical stimulus and a pair of electrodes configured to apply the electrical stimulus to the at least one of the soft palate or uvula.

16. The method of claim 14, further comprising activating the microstimulator in a temporal pattern to deliver the electrical stimulation to the at least one of the soft palate or the uvula to cause at least one muscle to contract, wherein the temporal pattern includes periods of an absence of electrical stimulation to permit the at least one muscle to cease from contracting.

17. The method of claim 14, further comprising observing at least one of the uvula or soft palate to determine the intensity which decreases the vibration of the uvula or soft palate.

18. The method of claim 17, wherein the electrical stimulation is of an intensity within a range of about 8 to about 800 nC.

19. The method of claim 14, further comprising sensing when snoring is occurring, and electrically stimulating the at least one microstimulator implanted within the soft palate or the uvula in response to sensing snoring.

20. The method of claim 19, wherein snoring is sensed by detecting mechanical vibrations of at least on anatomical structure.

21. The method of claim 19, wherein snoring is sensed by acoustically detecting sounds generated by at least one vibrating anatomical structure in the airway passages.

22. The method of claim 1, wherein the anatomical structure is a Muscle selected from the group comprising: palatoglossus, palatopharyngeal, musculus uvulae, genioglossus, geniohyoid, levator palati or tensor palati.

23. The method of claim 1, wherein the anatomical structure is a branch or terminal of a nerve selected from the group comprising: vagus XI hypoglossal, vagus pharyngeal branch, V3 branch trigeminal nerve.

24. The method of claim 1, further comprising implanting a second microstimulator proximate to at least a second anatomical structure, different than the at least one anatomical structure.

25. The method of claim 24, wherein at least one anatomical structure and a second anatomical structure are muscle pairs selected from the group comprising: geniohyoid and genioglossus; tensor palati and palatoglossus; tensor palati and musculus uvulae.

26. The method of claim 24, wherein at least one of the Microstimulators includes a sensor and a telemeter configured to generate a signal indicative of a sensed condition, and at least one of the microstimulators includes a circuitry configured to generate an electrical stimulation pulse.

27. The method of claim 1, wherein the microstimulator is implanted in a muscle selected from the group comprising: palatoglossus, palatopharyngeal, or musculus uvulae.

28. The method of claim 1, wherein the microstimulator is implanted proximate to a branch or terminal of the vagus X nerve.

29. The method of claim 1, further comprising implanting a second microstimulator in the proximity of an anatomical structure selected from the group comprising: palatoglossus, palatopharyngeal, musculus uvulae, genioglossus, geniohyoid, levator palate, tensor palati, vagus X, hypoglossal, vagus pharyngeal branch, V3 branch trigeminal nerve.

30. The method of claim 1, further comprising:
a) inserting the distal tip of the injection tool including a microstimulator through the oral mucosa of the soft palate;
b) inserting the distal tip of the injection tool into the uvula;
c) activating the injection tool to deposit the microstimulator from the injection tool; and
d) removing the insertion tool from the uvula.

31. The method of claim 30, further comprising positioning the microstimulator in or in the proximity of the musculus uvulae.

32. The method of claim 30, further including positioning the microstimulator in the proximity of the terminal branches of the motor axons to the musculus uvulae, wherein the microstimulator includes a cathode and an anode; and positioning the microstimulator cathode in the proximity of the terminal branches of the motor axons to the musculus uvulae.

33. The method of claim 30, further comprising advancing a distal tip of an insertion tool through the oral mucosa to the soft palate to the uvula, wherein the distal tip of the insertion tool includes a microstimulator within a lumen of the distal tip; and testing microstimulator by emitting electrical stimulation from the microstimulator within the lumen of the distal tip; and withdrawing the insertion tool leaving the microstimulator within the uvula.

34. The method of claim 1, further comprising applying electrical stimulations for a selected duration to stimulate at least the first muscle in the oropharynx to contract, and interrupting the electrical stimulation for a selected duration at a selected period to permit the first muscle in the oropharynx to relax.

35. The method of claim 1, further comprising transmitting from a controller to the microstimulator power, control signals, or power and control signals.

36. The method of claim 1, further comprising transmitting an acknowledgement signal from the microstimulator to a controller, wherein the acknowledgement signal indicates that the microstimulator has received a control signal from a controller.

37. The method of claim 1, further comprising alternately stimulating a first and a second muscle in the oropharynx to contract so that the airway passage remains substantially free of vibrating soft tissue during sleep.

38. The method of claim 37, further comprising selecting a pattern of stimulation such that while the first muscle is being contracted the second muscle may have a period of relaxation, and while the second muscle is being contracted, the first muscle may have a period of relaxation.

39. The method of claim 37 wherein the first and second muscles are selected from the group comprising: palatoglossus, palatopharyngeal, musculus uvulae, genioglossus, geniohyoid, levator palati, tensor palati.

40. The method of claim 37, wherein the first and second muscles are selected from the groups of pairs comprising: tensor palati and palatoglossus; tensor palati and musculus uvulae; and geniohyoid and genioglossus.

41. The method of claim 37, further comprising:
  a) sensing when snoring is occurring; and
  b) generating an electrical stimulus from the microstimulator to contract an oropharyngeal muscle, in response to sensing snoring in step a).

42. The method of claim 41, wherein snoring is sensed by detecting mechanical vibrations of at least one anatomical structure.

43. The method of claim 41, wherein snoring is sensed by acoustically detecting sounds generated by the at least one vibrating anatomical structure in the airway passages.

44. The method of claim 41, further comprising implanting a first microstimulator and a second microstimulator, and wherein the first and second microstimulators are alternately activated to cause the contraction of the at least first and second muscle in the oropharynx.

45. The method of claim 44, further comprising alternately applying electrical stimulations of an intensity from about 8 to about 800 nC to stimulate the first and second muscle in the oropharynx to contract.

46. The method of implanting a microstimulator into the genioglossus muscle comprising:
  a) inserting an imaging device into the airway passage of a patient;
  b) introducing an injection tool carrying at least one microstimulator through the epidermis under the mandible;
  c) passing the distal tip of the injection tool through the geniohyoid muscle;
  d) advancing the distal tip of the injection tool into the genioglossus muscle;
  e) energizing the microstimulator to electrically stimulate the genioglossus muscle;
  f) observing, with the imaging device, whether the stimulation causes a decrease in vibration of tissue in the airway passage;
  g) depositing, if a decrease in vibration of the tissue is observed, the microstimulator in the genioglossus muscle; and
  h) removing the insertion tool from the body.

47. The method of claim 46, further comprising positioning the microstimulator in the proximity of the endplate zone of the radially oriented sagittal muscle fibers of the genioglossus muscle, wherein the microstimulator includes a cathode and an anode; and positioning the microstimulator cathode in the proximity of the endplate-zone of the radially oriented sagittal muscle fibers of the genioglossus muscle.

* * * * *